United States Patent [19]

Sjoerdsma et al.

[11] Patent Number: 5,196,450
[45] Date of Patent: Mar. 23, 1993

[54] METHOD OF INHIBITING PROTOZOAL GROWTH

[75] Inventors: Albert Sjoerdsma, Cincinnati, Ohio; Peter P. McCann, Lebanon, Ind.; Philippe Bey, Cincinnati; Patrick J. Casara, Fairfield, both of Ohio

[73] Assignee: Merrell Dow Pharmaceuticals Inc., Cincinnati, Ohio

[21] Appl. No.: 768,789

[22] Filed: Sep. 30, 1991

Related U.S. Application Data

[63] Continuation of Ser. No. 453,011, Dec. 20, 1989, abandoned, which is a continuation of Ser. No. 330,967, Mar. 28, 1989, abandoned, which is a continuation of Ser. No. 205,039, Jun. 7, 1988, abandoned, which is a continuation of Ser. No. 930,055, Sep. 2, 1987, abandoned, which is a continuation of Ser. No. 931,591, Nov. 25, 1986, abandoned, which is a continuation-in-part of Ser. No. 811,147, Dec. 19, 1985, abandoned.

[51] Int. Cl.$^5$ ............................................. A61K 31/195
[52] U.S. Cl. .................................... 514/565; 514/634; 562/560; 564/240; 560/168

[58] Field of Search ................. 560/168; 562/560; 564/240; 514/599, 550, 565, 634

[56] References Cited

U.S. PATENT DOCUMENTS

| | | | |
|---|---|---|---|
| 4,134,918 | 1/1979 | Bey | 564/240 |
| 4,139,563 | 2/1979 | Metcalf | 564/240 |
| 4,182,891 | 1/1980 | Metcalf | 562/561 |
| 4,267,374 | 5/1981 | Metcalf | 564/240 |
| 4,309,442 | 1/1982 | Bey | 514/564 |
| 4,325,961 | 4/1982 | Kollonitsch | 560/40 |
| 4,413,141 | 11/1983 | Bey | 562/561 |
| 4,423,073 | 12/1983 | Gerhart | 562/561 |
| 4,439,619 | 3/1984 | Bey | 562/561 |
| 4,446,151 | 5/1984 | Gerhart | 562/561 |
| 4,454,156 | 6/1984 | Casara | 562/574 |

Primary Examiner—Michael L. Shippen
Attorney, Agent, or Firm—Neal O. Willmann

[57] ABSTRACT

This invention relates to the use of α-halomethyl, α-acetylenic or α-allenic derivatives of arginine and agmatine, or their dehydro analogs, in the treatment of Chagas disease and Coccidiosis.

11 Claims, No Drawings

METHOD OF INHIBITING PROTOZOAL GROWTH

This is a continuation of application Ser. No. 07/453,011, filed Dec. 20, 1989, now abandoned, which is a continuation of Ser. No. 07/330,967, filed Mar. 28, 1989, now abandoned, which is a continuation of application Ser. No. 205,039, filed Jun. 7, 1988, now abandoned, which is a continuation of application Ser. No. 930,055, filed Sep. 2, 1987, abandoned, which is a continuation of application Ser. No. 931,591, filed Nov. 25, 1986, abandoned, which is a continuation in part of application Ser. No. 811,147, filed Dec. 19, 1985, abandoned.

This invention relates to the use of certain irreversible enzyme inhibitors which interrupt the biosynthesis of polyamines and which inhibit the growth of certain protozoans.

More specifically this invention relates to certain agmatine and arginine derivatives which are enzyme inhibitors useful in the treatment of animals suffering from disease states caused by parasitic infections with certain protozoa.

Still more specifically, this invention relates to X-substituted arginine and agmatine compounds having the formula

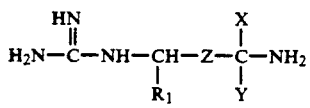

their pharmaceutically acceptable salts, their individual optical isomers and mixtures thereof, wherein $R_1$ is H or $CH_3$, Z is $-CH_2-CH_2-$ or $-CH=CH-$, X is $-CH_2F$, $-CHF_2$, $-CHCl_2$, $-CHClF$, $-C\equiv CH$ or $-CH=C=CH_2$, Y is H or COOR with R being H or $C_{1-18}$ alkyl, which compounds are enzyme inhibitors useful in the treatment of certain disease states in animals, including man, said disease states being caused by infection of the animals with certain protozoa. In those instances wherein Z is $-CH=CH-$, the double bond preferably is in its trans configuration, i.e. the (E) designated compound.

In essence the compounds depicted by formula I are halomethyl, acetylenic, or allenic derivatives of arginine and agmatine or their dehydro derivatives. For the most part these compounds are known and their preparation is adequately described in the prior art. In those specific instances wherein the compounds are novel, per se, such compounds may be prepared by methods and techniques analogously known in the art. For example, the halomethyl derivatives of the amines (i.e. Y is H and Z is $-CH_2-CH_2-$) may be prepared by the techniques of U.S. Pat. No. 4134918, and the dehydro analogs thereof by using the techniques of British Patent No. 2083030 and with the techniques hereinbelow illustrated by Examples 1-3. The halomethyl derivatives of the α-amino acids (i.e. Y is COOR) may be prepared by the teachings of South African Patent No. 78/3349 and their dehydro derivatives may be prepared by the teachings of British Patent No. 2083030. The acetylenic derivatives of the amino acids (i.e. Y is COOR and X is $-C\equiv CH$) may be prepared by the teachings of U.S. Pat. No. 4182891 and of the amines (i.e. Y is H and X is $C\equiv CH$) may be prepared by the teachings of 4139563. The allenic derivatives of the compounds of formula I may be prepared from the acetylenic derivatives by the techniques of U.S. Pat. No. 4,454,156 which are further elaborated upon by Casara in Tetrahedron Letters, Vol. 25, pg. 1891 (1984).

The technique for selectively converting an amino moiety to a guanidino moiety is illustrated by the following specific examples. This technique is generally available to make compounds of formula I from intermediates which are analogous to those used in these examples.

EXAMPLE 1

1-Guanidino-4-amino-5-hexyne dihydrochloride

Triethylamine (4.5 ml, 30 mmoles) is added to a solution of 1,4-diamine-5-hexyne dihydrochloride (1.85 g, 10 mmoles) in water (50 ml) at $-10°$ C. To this solution 3,5-dimethylpyrazole-1-carboxamidine nitrate (2.3 g, 10.5 mmoles) is slowly added (in small portions) and the resulting mixture is stirred 2 h at $-10°$ C., and for 3 days at room temperature after all starting materials have reacted (this is controlled by electrophoresis and ninhydrin colorimetric analysis). Then, the mixture is acidified (pH 5-6) with a 1 M solution of HCl and washed with dichloromethane (2×100 ml). The aqueous layer is concentrated under reduced pressure to a volume of 5 ml. This concentrated mixture is purified by ion exchange chromatography. (DOWEX 50W-X8, 100-200 mesch, H+Form) which is eluted by using a gradient of solution of HCl (0 to 4 N). The eluted fractions are checked by electrophoresis on silica gel plates and colorimetric analysis (ninhydrin and Sakaguchi reagent). The fractions containing the guanidino material are concentrated together under reduced pressure to give the title compound (1.7 g) as a colorless oil. NMR($^1$H) δ ppm. 1.76 (m, 4H); 2.96 (d,1H,J=1H$_2$); 3.16 (m, 2H) 4.2 (m, 1H). M/Z: MH+ 155; MH± NH$_3$: 138; MH± NH$_2$—CNHNH$_2$=98.

EXAMPLE 2

1-Fluoro-2-amino-5-guanidinopentane dihydrochloride

Using the procedure similar to that described in the first example 1-fluoro-2,5-diaminopentane dihydrochloride (1.93 g, 10 mmoles) afforded 1.9 g of the title compound, mp: 158° C. after recrystallization from ethanol/ether.

Similarly, using the procedure similar to that described in the first example, 4,7-diamino-1,2-heptadiaene dihydrochloride (2.0 g, 10 mmole) afforded 2.1 g of 4-amino-7-guanidino-1,2-heptadiene dihydrochloride as an oil.

EXAMPLE 3

(E)α-Fluoromethyl-3,4-dehydro arginine monohydrochloride

Using the procedure similar to that described in example one (E)- -fluoromethyl-3,4-dehydro ornithine monohydrochloride (1.8 g, 10 mmole) in 50 ml of water, triethylamine (3 ml, 20 mmoles) and 3,5-dimethylpyrazole-1-carboxamidine nitrate (2.5 g, 1.1 mmoles) yielded, after two weeks at room temperature, 2.2 g of the title compound as a white solid, which was recrystallized from absolute EtOH (mp 171° C., decomp.). H$_1$NMR Data: (D$_2$O, DCl) ($^1$H) δ (ppm) 4.0 (d, 2H) 4.65 (q, 1H), 5.25 (q, 1H) 5.75 (m, 2H)

Using the procedure similar to that described in example three, α-fluoromethyl ornithine monohydrochloride (2.0 g, 10 mmoles) afforded 2.05 g of α- fluoromethyl arginine monohydrochloride, mp 190° C. after recrystallized from absolute EtOH.

In a similar manner, by following the teachings set forth above in examples 1-3 and by following the teachings set forth in the above cited prior art the following compounds may also be prepared:

α-difluoromethyl-3,4-dehydro arginine;
α-fluoromethyl-2,3-dehydro agmatine;
α-difluoromethyl-2,3-dehydro agmatine;
α-acetylenic-3,4-dehydro arginine;
α-acetylenic-2,3-dehydro agmatine;
α-allenyl-3,4-dehydro arginine; and
α-allenyl-2,3-dehydro agmatine.

Illustrative examples of the salts of the compounds of this invention include non-toxic acid addition salts formed with inorganic acids, such as, hydrochloric, hydrobromic, sulfuric and phosphoric acid, and organic acids, such as, methanesulfonic, salicyclic, maleic, malonic, tartaric, citric, cyclamic and ascorbic acids. In addition to the salts indicated above, the term salts is taken to include those internal salts or zwitter-ions of those compounds of formula (I) above that are amphoteric in nature. Moreover, whereas the optical configuration for the compounds described herein is not specifically designated, it is recognized that the α-carbon atom possesses an asymmetric center and that individual optical isomers of these compounds exist. Accordingly, both the D- and L-optical isomers as well as the racemic mixtures are contemplated as being within the scope of this invention.

As stated above, the derivatives of arginine and agmatine of formula I are irreversible inhibitors which are capable of interrupting the biosynthesis of polyamines and which are now found to be useful in the treatment of diseases caused by parasitic infections with certain protozoa.

The rationale of polyamine metabolism has been suggested by Cohen, Science, 205, p 964 (1974). Impairment of the biosynthesis of polyamines by means of enzyme inhibitors also has been known to cause a decrease in cell proliferation in animals. Although the physiological role of the polyamines has not yet been clearly delineated, some evidence suggests their involvement with cell division and rapid cell growth. (H. S. Williams-Ashman et al., The Italian J. Biochem. 25, 5-32 (1976), A. Raina and J. Janne, Med. Biol. 53, 121-147 (1975) and D. H. Russell, Life Sciences 13, 1635-1647 (1973)). Indeed, there is evidence suggesting that polyamines are associated with both normal and rapid proliferative mammalian cell growth; their being an increase in both the synthesis and accumulation of polyamines following a stimulus causing cell growth.

Polyamines are also known to be essential growth factors in non-mammalians, particularly in such microorganisms as, for example, *E. Coli*, Enterobacter, Klebsiella, *Staphylococcus Aureaus*, *C. cadaveris*, *Salmonelle typhosa* and *Hemophilus pareinfluenza*.

It is further known by the teachings of U.S. Pat. No. 4399151 that the growth of certain protoza has been inhibited with ornithine decarboxylase inhibitors. Indeed, the ornithine decarboxylase inhibitors have been shown to be useful in the treatment of African sleeping sickness (caused by *Trypanosoma brucei rhodesiense* and *Trypanosoma brucei gambiense*) and in the treatment of coccidiosis (caused by *Eimeria tenella*). Quite surprisingly, these same ornithine decarboxylase inhibitors were found to be ineffective in the treatment of other diseases caused by infection with other Trypanosoma.

Notable amongst these disease states not controlled by ornithine decarboxylase inhibitors are Chagas disease and coccidiosis caused by species of Eimeria other than tenella.

Therefore, throughout this application and in the context of the generic scope of this invention the term "protozoa" is intended to include those members of the subphyla Sarcomastigophora and Sprozoa of the phylum Protozoa. More particularly, the term "protozoa" as used herein is intended to include those genera of parasitic protozoa which are important to man because they either cause disease in man or his domestic animals. These genera are for the most part found classified in the superclass of Mastigophora of the subphylum Sarcomastigophora and the class of Telosporea of the subphylum Sporozoa in the classification according to Baker (1969). Illustrative genera of these parasitic protozoa include Trypanosoma, Giardia, Eimeria, Toxoplasma, Entamoeba, Babesia and Theilera.

Specifically excluded from the scope of protozoa of this invention are those members of the genus Trypanosoma of the subsection Salivaria which subsection includes such species as rhodesiense, qambiense, brucei, evansi, equinum, simiae, equiperdum, conqolese and vivax. Also excluded are those species of the genus Plasmodium and the specie tenella of the genus Eimeria; the latter species being responsible for certain forms of coccidiosis in poultry.

Specifically included within the term "protozoa" of this invention are those members of the genus Trypanosoma which belong to the subsection Stercoraria (which subsection includes the members of the subgenera Megatrypanium, Herpetosoma and Schizotrypanum), Leishmania, Entamoeba, Eimeria, Toxoplasma, Babesis and Theileria. Representative species of the foregoing genera included within the scope of this invention are *T.(S)cruzi*, *T.(H.)lewisi*, *T.(H.)musculi*, *T.(H.)rangeli* and *T.(M.)theileri*; *B. bovis*, *B. rodhaini*, *B. microti*, *Theileria parva*, *Toxoplasma gandii*, *Eimeria necratrix* and *brunetti*, *Entemoeba histolytica* and *invadens*.

Perhaps the most important disease states caused by the parasitic infections with the above defined protozoa are Chagas Disease and Coccidiosis (in poultry).

The protozoan parasite *Trypanosoma cruzi* is the etiologic agent of Chagas disease which is endemic to vast areas of South and Central America. It is a particularly dreadful disease not only because of the severe acute and chronic debilitating symptoms suffered by millions, but also because there is no known effective treatment. Thus, the use of the compounds of formula I in the prevention and treatment of the disease and in the control of the causative parasite is, indeed, a significant advance.

In the use of the compounds of the compounds of this invention as anti-protozoal agents, the relative potencies of the enzyme inhibitory properties may readily be determined by standard in vitro laboratory techniques. Standard in vivo evaluations may also be effected (however, because of the lack of an effective chemotherapeutic agent to control the protozoa, difficulty is experienced in finding suitable laboratories in the United States which routinely conduct such procedures). However, based on the early data, it is expected that effective treatment is about 0.5 gm to 5 gm per kilogram of body weight per day. In those particularly severe cases, because of the relative low toxicity of these compounds, it is expected that initial therapy may be as high as 8 gm per kilogram of body weight per day. Treatment most preferably is with 2% aqueous formulations, preferably by infusion at early treatment stages and by standard pharmaceutical formulations at a later stage. In the treatment of coccidiosis it is preferred to administer the compounds in the drinking water of the poultry infected with the disease.

In addition to the foregoing methods of treating "patients" suffering from the disease states caused by the parasitic infections with the above defined protozoa, it is also advantageous to control the spread of the disease with prophylactic techniques. For example, not only has the spread of Chagas disease been associated with the metacyclic tryptomastigotes present in the fecal fluids of insect vectors, but also through the blood administered in blood transfusions. Thus, the patients receiving blood transfusions may receive prophylactic treatment but also the blood, per se, may be pre-treated with the compounds of formula I in order to eliminate this source of parasitic infection.

Another way to advantageously administer compounds of this invention is to administer combinations of the compounds of this invention, preferably administering one member of the group of compounds defined by formula I wherein Y is other than H, and another member wherein Y is hydrogen, i.e. a combination of an arginine derivative and an agmatine derivative.

In addition to the foregoing method of use for the compounds of this invention, it is also advantageous to use compounds of this invention in combination with ornithine decarboxylase inhibitors in the treatment of coccidiosis, particularly when the poultry may have parasitic infections with different species of Eimeria, e.g., infections with *Eimeria tenella* and *Eimeria necratrix*.

The compounds of formula I may be formulated for use as anti-protozoal agents according to standard prior art teachings. Preferably use of physiological solutions having about 2% of the compounds of formula I may be useful for infusion, or more concentrated solutions may be used in drinking water. Other formulations, the preparation of which is well known in the art, may be used. Formulations and techniques, such as those disclosed in U.S. Pat. No. 4399151 may be used in the treatment of coccidiosis.

As is true for most classes of compounds found useful as chemotherapeutic agents certain sub-classes and certain species are preferred. In this instance those compounds wherein X represents a halomethyl (mono- or di-) are most preferred, those compounds wherein Z is either saturated or unsaturated are preferred, those compounds wherein Y is a COOH moiety are preferred over their ester derivatives. Conjunctive therapy with the preferred arginine derivatives and the preferred agmatine derivatives is also preferred. A preferred X and/or Z- modified arginine or agmatine compound is also preferred. Specifically preferred species are:

α-fluoromethyl arginine and its 3,4-dehydro analog,
α-difluoromethyl arginine and its 3,4-dehydro analog,
α-fluoromethyl agmatine and its 2,3-dehydro analog,
α-difluoromethyl agmatine and its 2,3-dehydro analog,
α-acetylenic agmatine,
α-acetylenic arginine and
α-allenyl agmatine.

We claim:

1. A method of inhibiting the growth of the protazoa *Trypanosoma cruzi* which comprises administering protazoal inhibiting amounts of an X-substituted arginine or agmatine of the formula

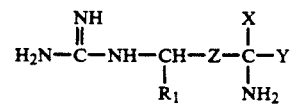

and the pharmaceutically acceptable salts thereof, the individual and racemic mixtures of their optical isomers, wherein $R_1$ is h or $CH_3$
Z is $-CH_2-CH_2-$ or $-CH=CH-$, X is $-CH_2F$, $-CHF_2$, $CHCl_2$, $-CHClF$, $-C\equiv CH$ or $-CH=C=CH_2$
Y is H or COOR with R being H or $C_{1-18}$ lower alkyl.

2. A method of treating an animal suffering from Chagas Disease which comprises administering to said animal a protozoal inhibiting amount of a compound defined in claim 1.

3. A method according to claim 2 wherein the X moiety of the compound utilized is a halomethyl moiety.

4. A method of claim 3 wherein X is fluoromethyl.

5. A method of claim 3 wherein X is difluoromethyl.

6. A method of claim 3 wherein the compound is an arginine derivative.

7. A method of claim 3 wherein the compound is an agmative derivative.

8. Compounds of the formulae

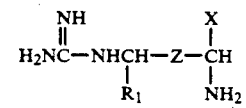  A

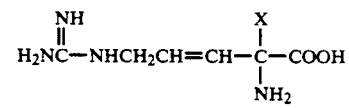  B the individual optical isomer and mixtures thereof, wherein

X is $-CH_2F$, $-CHF_2$ or $-CH=C=CH_2$,
Z is $-CH_2-CH_2-$ or $-CH=CH-$,
and $R_1$ is hydrogen, with the proviso that when Z is $-CH_2-CH_2-$, X is $-CH=C=CH_2$.

9. A compound of claim 8 wherein X is $-CH_2F$ or $-CHF_2$.

10. A compound of claim 8 wherein X is $-CH=C=CH_2$.

11. Compounds of claim 8 wherein the double bond is in its trans configuration.

* * * * *